United States Patent [19]
Perry

[11] Patent Number: 6,066,643
[45] Date of Patent: *May 23, 2000

[54] POTENTIATION OF PHARMACEUTICALS

[75] Inventor: Kenneth Wayne Perry, Indianapolis, Ind.

[73] Assignee: Eli Lilly and Company, Indianapolis, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/169,369

[22] Filed: Oct. 9, 1998

Related U.S. Application Data

[60] Provisional application No. 60/062,282, Oct. 17, 1997.

[51] Int. Cl.[7] .................... A61K 31/505; A61K 31/445; A61K 31/135
[52] U.S. Cl. ................... 514/269; 514/317; 514/651
[58] Field of Search ................. 514/269, 651, 514/317

[56] References Cited

U.S. PATENT DOCUMENTS

| | | | |
|---|---|---|---|
| 4,952,410 | 8/1990 | Armah et al. | 424/465 |
| 5,552,429 | 9/1996 | Wong et al. | 514/415 |
| 5,712,283 | 1/1998 | Kaan et al. | 514/269 |

OTHER PUBLICATIONS

Michael Bourin, et.al., "Clonidine As a Sensitizing Agent in the Forced Swimming Test for Revealing Antidepressant Activity", *J Psychiatr Neurosci,* vol. 16, No. 4, pp. 199–203 (1991).

John E. Piletz and Angelos Halaris, "Involvement of $I_1$–Imidazoline Receptors in Mood Disorders", *Annals New York Academy of Science,* vol. 763, pp. 510–519, (1995).

M. Hascoet, et.al., "Behavioral models in mice. Implication of the alpha noradrenergic system", *Prog. Neuropsychopharmacol Biol Psychiatry,* 15 (6), pp. 825–840 (1991) (Abstract).

M. Hascoet, et.al., "Additive effect of lithium and clonidine with 5–HT1A agonists in the forced swimming test", *Prog Neuropsychopharmacol Biol Psychiatry,* 18 (2), pp. 381–396 (1994) (Abstract).

J.P. Redrobe and M. Bourin, "Effects of pretreatment with clonidine, lithium and quinine on the activites of antidepressant drugs in the mouse tail suspension test", *Fundam Clin Pharmacol,* 11 (5), pp. 381–386 (1997) (Abstract).

T.F.Meert and M. De Kock, "Potentiation of the analgesic properties of fentanyl–like opioids with alpha 2–adrenoceptor agonists in rats"., *Anesthesiology,* 81 (3), pp. 677–688, September (1994) (Abstract).

V. Jevtovic–Todorovic, et.al., "Clonidine potentiates the neuropathic pain–relieving action of MK–801 while preventing its neurotoxic and hyperactivity side effects", *Brain Res,* 781 (1–2), pp. 202–211, (1998) (Abstract).

Y.W. Lee and T.L. Yaksh, "Analysis of drug interaction between intrathecal clonidine and MK–801 in peripheral neuropathic pain rat model", *Anesthesiology,* 82 (3), pp. 741–748, March (1995) (Abstsract).

T.F. Mert and M. De Kock, "Interactions between the lipophilic opioid sufentanil and clonidine in rats after spinal application", *Acta Anaesthesiol Scand,* 39 (4), pp. 527–534, May (1995) (Abstract)

S. Hedges, et.al., "Clonidine does not potentiate the antipsychotic effects of neuroleptics in chronically ill patients", *Ann Clin Psychiatry,* 10 (1), pp. 3–7, March (1998) (Abstract).

N.J. Carrey, et.al., "Pharmacological treatment of psychiatric disorder in children and adolescents: focus on guidelines for the primary care practitioner", *Drugs,* 51 (5), pp. 750–759, May (1996) (Abstract).

*Primary Examiner*—Raymond Henley, III
*Attorney, Agent, or Firm*—Scott Alexander McNeil; John C. Demeter

[57] ABSTRACT

The present invention provides a method for producing a potentiating effect on a therapeutic action of an agent which is selected from a serotonin re-uptake inhibitor, a norepinephrine re-uptake inhibitors, both a serotonin and norepinephrine re-uptake inhibitor, and an atypical antidepressant in a warm blooded mammal, which comprises administering to said mammal an effective amount of moxonidine, or a pharmaceutically acceptable salt thereof.

28 Claims, No Drawings

POTENTIATION OF PHARMACEUTICALS

This application claims the benefit of U.S. Provisional Application No. 60/062282, filed Oct. 17, 1997.

The present application relates to the potentiation of pharmaceuticals. More particularly it relates to the use of a compound to produce a potentiating effect on a therapeutic action of an agent which is selected from a serotonin re-uptake inhibitor, a norepinephrine re-uptake inhibitors, both a serotonin and norepinephrine re-uptake inhibitor, and an atypical antidepressant.

Serotonin re-uptake inhibitors, norepinephrine re-uptake inhibitors, and both serotonin and norepinephrine re-uptake inhibitors each form a well known therapeutic class of compounds which are useful for the treatment of central nervous system disorders, such as depression. While such agents and the atypical antidepressants such as nefazodone, mirtazepine and bupropion have found widespread acceptance by the medical community, it has been found that their onset of action, as measured by the time for them to take effect, can be slow (typically about 4–6 weeks), and their overall effectiveness, as measured by the percentage of people responding moderately well to treatment with them, is modest (typically no more than 65%) and as measured by people fully remitting is low (30–40%).

Bourin et al, *J. Psychiatr. Neurosci*, 16, No. 4, 1991, pages 199 to 203 discloses that the compound clonidine increases the sensitivity of a test for antidepressant activity known as Porsolt's forced swimming test. However, clonidine, which is used for the treatment of hypertension, has not been found to be useful for the treatment of depression, and indeed is contra-indicated for use in depressed patients.

Another compound which is used for the treatment of hypertension is moxonidine. It has the chemical name 4-chloro-6-methoxy-2-methyl-5-(2-imidazolin-2-yl)amino-pyrimidine and is described together with its pharmaceutically acceptable salts in U.S. Pat. No. 4,323,570. Like clonidine, moxonidine is contra-indicated for use in depressed hypertensive patients. Both compounds are thought to be agonists at alpha-2 adreno-receptors and imidazoline 1 ($I_1$) receptors, but moxonidine, unlike clonidine, is thought to be selective for $I_1$ receptors (D. J. Nutt et al., Annals New York Academy of Sciences, 125–139, 1995). This difference in selectivity between the two compounds is reflected in a difference in the side-effect profiles of the two compounds. In particular, clonidine is associated with drowsiness, headache, dry mouth and nasal congestion, all of which are thought to be connected with its alpha-2 adrenoreceptor activity. These side effects are seen with substantially lower frequency with moxonidine at doses effective in the treatment of hypertension, and when seen generally subside early in a course of treatment with the compound.

The present invention provides a method for producing a potentiating effect on a therapeutic action of an agent which is selected from a serotonin re-uptake inhibitor, a norepinephrine re-uptake inhibitors, both a serotonin and norepinephrine re-uptake inhibitor, and an atypical antidepressant in a warm blooded mammal, which comprises administering to said mammal an effective amount of moxonidine, or a pharmaceutically acceptable salt thereof.

According to another aspect, the present invention provides the use of moxonidine, or a pharmaceutically acceptable salt thereof in the manufacture of a medicament for producing a potentiating effect on a therapeutic action of an agent selected from a serotonin re-uptake inhibitor, a norepinephrine re-uptake inhibitors, both a serotonin and norepinephrine re-uptake inhibitor, and an atypical antidepressant.

According to yet another aspect, the present invention provides a pharmaceutical composition of moxonidine, or a pharmaceutically acceptable salt thereof for use in producing a potentiating effect on a therapeutic action of an agent which is selected from a serotonin re-uptake inhibitor, a norepinephrine re-uptake inhibitors, both a serotonin and norepinephrine re-uptake inhibitor, and an atypical antidepressant.

In the method or a use (hereinafter referred to as the method) according to the invention, the potentiating effect may be an efficacy enhancing effect or an onset enhancing effect, or both.

The therapeutic action potentiated by moxonidine may be one or more of a known therapeutic action of the compound selected from an antidepressant, antibulimia, antipremenstrual syndrome, antiobsessive-compulsive disease, antiobesity or antiurinary incontinence action. A preferred therapeutic action is an antidepressant action.

Depression can be characterized by extreme feelings of sadness, dejection, lack of worth, or emptiness, loss of pleasure in once pleasurable activities, change in sleep patterns, forgetfulness, lack of concentration, change in appetite, decrease in physical activity, lack of energy, feelings of hopelessness, or suicidal thoughts or tendencies. Common causes of depression include loss of friend or relative, substantial disappointment at home or work, prolonged or chronic illness, drugs (such as tranquilizers, high blood pressure medicines, steroids, codeine, and indomethacin), alcohol intoxication, alcohol withdrawal, drug intoxication, and drug withdrawal.

Pharmaceutical agents used in treating depression include amitriptaline, clomipramine, doxepin, imipramine, (+)-trimipramine, amoxapine, desipramine, maprotiline, nortriptyline, protriptyline, (±)-fluoxetine, fluvoxamine, paroxetine, sertraline, (±)-venlafaxine, bupropion, nefazodone, and trazodone.

Bulimia is characterized by recurrent episodes of binge eating, recurrent inappropriate compensatory behavior in order to prevent weight gain; such as self induced vomiting, misuse of laxatives, diuretics, enemas, or other medications, fasting, or excessive exercise. An episode of binge eating is characterized by both of the following: 1) eating in a discrete period of time an amount of food that is definitely larger than most people would eat during a similar period of time and under similar circumstances, and 2) a sense of lack of control over eating during the episode. Menstrual irregularity or amenorrhea sometimes occurs among females with bulimia; whether such disturbances are related to weight fluctuations, to nutritional deficiencies or to emotional stress is uncertain.

Pharmaceutical agents used in treating bulimia include amitriptaline, clomipramine, doxepin, imipramine, (+)-trimipramine, amoxapine, desipramine, maprotiline, nortriptyline, protriptyline, (±)-fluoxetine, fluvoxamine, paroxetine, sertraline, and (±)-venlafaxine.

Premenstrual syndrome is a symptom or collection of symptoms that occurs regularly in relation to the menstrual cycle, with the onset of symptoms 5 to 11 days before the onset of menses and resolution of symptoms with menses or shortly thereafter. The most common of symptoms include headache, swelling of ankles, feet and hands, backache, abdominal cramps or heaviness, abdominal pain, abdominal fullness or gas, muscle spasms, breast tenderness, weight gain, recurrent cold sores, acne flare-up, nausea, bloating, constipation or diarrhea, decreased coordination, food cravings, decreased tolerance to sensory input, painful menstruation, anxiety, confusion, difficulty concentrating, forgetfulness, depression, irritability, fatigue, libido changes, paranoia, and low self-esteem.

Pharmaceutical agents used in treating premenstrual syndrome include amitriptaline, clomipramine, doxepin, imipramine, (+)-trimipramine, amoxapine, desipramine, maprotiline, nortriptyline, protriptyline, (±)-fluoxetine, fluvoxamine, paroxetine, sertraline, (±)-venlafaxine, bupropion, nefazodone, and trazodone.

Features of Obsessive-Compulsive Disorder are recurrent obsessions or compulsions that are severe enough to be time consuming or cause marked distress or significant impairment. At some point during the course of the disorder, the person has recognized that the obsessions or compulsions are excessive or unreasonable. The disturbance is not due to the direct physiological effects of a substance or a general medical condition.

Obsessions are persistent ideas, thoughts, impulses, or images that are experienced as intrusive and inappropriate and that cause marked anxiety or distress. The intrusive and inappropriate quality of the obsessions has been referred to as "ego-dystonic." This refers to the individual's sense that the content of the obsession is alien, not within his or her own control, and not the kind of thought that he or she would expect to have. However, the individual is able to recognize that the obsessions are the product of his or her own mind and are not imposed from without.

The most common obsessions are repeated thoughts about contamination, repeated doubts, a need to have things in a particular order, aggressive or horrific impulses, and sexual imagery. The thoughts, impulses or images are not simply excessive worries about real-life problems and are unlikely to be related to a real-life problem.

Pharmaceutical agents used in treating Obsessive Compulsive Disorder include clomipramine, (±)-fluoxetine, fluvoxamine, paroxetine, sertraline, and (±)-venlafaxine.

An individual is considered obese when weight is 20% (25% in women) or more over the maximum desirable for their height. Obesity increases the risk of illness and death due to diabetes, stroke, coronary artery disease, and kidney and gallbladder disorders. The more overweight, the higher the risk becomes. Causes of obesity include overeating, inadequate exercise, disease, and medication.

Pharmaceutical agents used in treating obesity include sibutramine.

Urinary incontinence is characterized by an involuntary loss of urine that occurs at the same time that internal abdominal pressure is increased, such as with coughing, sneezing, laughing, or physical activity. Urinary incontinence is a storage problem in which the urethral sphincter is not able to hold urine. Storage problems may occur as a result of weakened pelvic muscles that support the bladder, or malfunction of the urethral sphincter. Prior trauma to the urethral area, neurological injury, and some medications may weaken the urethral closure. Sphincter weakness may occur in men following prostate surgery or in women after pelvic surgery. Urinary incontinence may be seen in women who have had multiple pregnancies, pelvic prolapse, cystocele, or rectocele. Additionally, women with low estrogen levels may have urinary incontinence due to decreased vaginal muscle tone. Symptoms of urinary incontinence include sensation of bladder fullness, increased urinary frequency or urgency, perineal or vulvar discomfort, pain with intercourse, loss of urine with coughing, sneezing, standing, and physical activity, heavy menses or bleeding between menses, and painful bowel movements.

Pharmaceutical agents used in treating urinary incontinence include imipramine.

Serotonin re-uptake inhibitors represent a well known class of therapeutic agents. Compounds having serotonin re-uptake activity may be identified by the standard pharmacological assay described by Wong, et al., *Neuropsychopharmacology* 8, 337–344 (1993). Many compounds, including those discussed at length below, have such activity, and no doubt many more will be identified in the future. In the practice of the present invention, it is intended to include re-uptake inhibitors which show 50% effective concentrations of about 1000 nM or less, in the protocol described by Wong supra. Serotonin re-uptake inhibitors include, but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.* 31, 1412 (1988), taught the separation of the R and S enantiomers of fluoxetine and showed that their activity as serotonin uptake inhibitors is similar to each other. (It will be appreciated that in this specification, unless otherwise indicated, the generic name of a drug is used to signify a chemical compound and its pharmaceutically acceptable salts and enantiomeric forms. For example, the term "fluoxetine" will be used to include any acid addition salt, the free base, the racemic mixture and the separate R and S enantiomers);

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin re-uptake inhibitor. Its pharmacology was disclosed by Christensen et al., *Eur. J. Pharmacol.* 41, 153 (1977), and reports of its clinical effectiveness in depression may be found in Dufour et al., *Int. Clin. Psychopharmacol.* 2, 225 (1987), and Timmerman et al., ibid., 239;

Fluvoxamine, 5-methoxy-1-[4-(trifluoromethyl)-phenyl]-1-pentanone O-(2-aminoethyl)oxime, is taught by U.S. Pat. No. 4,085,225. Scientific articles about the drug have been published by Claassen et al., *Brit. J. Pharmacol.* 60, 505 (1977); and De Wilde et al., *J. Affective Disord.* 4, 249 (1982); and Benfield et al., *Drugs* 32, 313 (1986);

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan et al., *Brit. J. Clin. Pharmacol.* 19, 705 (1985); Laursen et al., *Acta Psychiat. Scand.* 71, 249 (1985); and Battegay et al., *Neuropsychobiology* 13, 31 (1985); and Sertraline, (1S-cis)-4-(3,4-dichlorophenyl)-1,2,3,4-tetrahydro-N-methyl-1-naphthylamine hydrochloride, is a serotonin re-uptake inhibitor which is marketed as an antidepressant. It is disclosed by U.S. Pat. No. 4,536,518.

Norepinephrine re-uptake inhibitors also represent a well known class of therapeutic agents. Compounds having norepinephrine re-uptake activity may be identified by the standard pharmacological assay described by Wong et al., *Drug Development Research*, 6, 397 (1985). In the practice of the present invention, it is intended to include re-uptake inhibitors which show 50% effective concentrations of about 1000 nM or less, in the protocol described by Wong supra. Many compounds, including those discussed at length below, have such activity, and no doubt many more will be identified in the future. Norepinephrine re-uptake inhibitors useful for the method of the present invention include, but are not limited to:

Tomoxetine, (R)-(−)-N-methyl-3-(2-methylphenoxy)-3-phenylpropylaminei is usually administered as the hydrochloride salt. Tomoxetine was first disclosed in U.S. Pat. No. 4,314,081. The word "tomoxetine" will be used here to refer to any acid addition salt and the free base of the molecule. See, for example, Gehlert, et al., *Neuroscience Letters*, 157, 203–206 (1993), for a discussion of tomoxetine's activity as a norepinephrine re-uptake inhibitor;

Reboxetine, disclosed in U.S. Pat. No. 4,229,449;

The compounds of formula I:

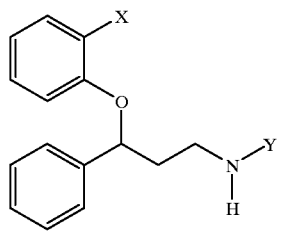

wherein X is $C_1$–$C_4$ alkylthio, and Y is $C_1$–$C_2$ alkyl or a pharmaceutically acceptable salt thereof. The compounds of formula I were described in U.S. Pat. No. 5,281,624, of Gehlert, Robertson, and Wong, and in Gehlert, et al., *Life Sciences*, 55(22), 1915–1920, (1995). The compounds are taught to be inhibitors of norepinephrine re-uptake in the brain. It is also disclosed that the compounds exist as stereoisomers, and that they accordingly include not only the racemates, but also the isolated individual isomers as well as mixtures of the individual isomers. For example, the compounds of formula I include the following exemplary species:

N-ethyl-3-phenyl-3-(2-methylthiophenoxy)propyl-amine benzoate;

(R)-N-methyl-3-phenyl-3-(2-propylthiophenoxy)-propylamine hydrochloride;

(S)-N-ethyl-3-phenyl-3-(2-butylthiophenoxy)propyl-amine;

N-methyl-3-phenyl-3-(2-ethylthiophenoxy)propyl-amine malonate;

(S)-N-methyl-3-phenyl-3-(2-tert-butylthiophenoxy)-propylamine naphthalene-2-sulfonate; and (R)-N-methyl-3-(2-methylthiophenoxy)-3-phenyl-propylamine.

Certain compounds are both a serotonin re-uptake inhibitor and a norepinephrine re-uptake inhibitor. Examples include:

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt and the free base of the molecule;

A Venlafaxine is known in the literature, and its method of synthesis and its activity as an inhibitor of serotonin and norepinephrine uptake are taught by U.S. Pat. No. 4,761,501. Venlafaxine is identified as compound A in that patent; and Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology* 24, 1211–19 (1985), describe its pharmacological activities as an inhibitor of serotonin and norepinephrine re-uptake.

The atypical antidepressants form a heterogeneous class. Examples include bupropion (1-(3-chlorophenyl)-2-[(1,1-dimethylethylamino]-1-propanone, disclosed in U.S. Pat. No. 3,819,706 and 3,885,046); nefazodone, (2-[3-[4-(3-chlorophenyl)-1-piperazinyl]propyl]-5-ethyl-2,4-dihydro-4-(2-phenoxyethyl)-3H-1,2,4-triazol-3-one, disclosed in U.S. Pat. No. 4,338,317); mirtazepine (1,2,3,4,10,14b-hexahydro- 2-methylpyrazino[2,1-a]-pyrido[2,3-c][2] benzazepine, disclosed in U.S. Pat. No. 4,062,848); and mianserin (1,2,3,4,10,14b-hexahydro-2-methyldibenzo[c,f] pyrazino-[1,2-a]azepine, disclosed in U.S. Pat. No. 3,534,041).

Preferably, the agent is selected from fluoxetine, citalopram, fluvoxamine, paroxetine, sertraline, tomoxetine, reboxatine, duloxetine, venlafaxine and milnacipran.

Fluoxetine is a particularly preferred agent in the method according to the invention.

According to a preferred aspect therefore, the present invention provides a method for the treatment of depression in a warm blooded mammal requiring treatment, which comprises administering an effective amount of fluoxetine and an effective amount of moxonidine.

In the methods according to the invention, the warm blooded mammal may be any warm blooded mammal, for example a rodent, dog, cat, primate or human. Preferably it is a human.

In general, moxonidine will be administered to the warm blooded mammal in a pharmaceutical composition comprising moxonidine and a pharmaceutically acceptable diluent or carrier. The pharmaceutical compositions may be prepared by known procedures using well-known and readily available ingredients. In making the compositions, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, micro-crystalline cellulose, polyvinylpyrrolidone, cellulose, water syrup, methyl cellulose, methyl and propyl hydroxy-benzoates, talc, magnesium stearate, and mineral oil. The formulations can additionally include lubricating agents, wetting agents, emulsifying and suspending agents, preserving agents, sweetening agents, or flavoring agents. Compositions may be formulated so as to provide quick, sustained, or delayed release of the active ingredient after administration to the patient by employing procedures well known in the art.

The following formulation example is illustrative only and is not intended to limit the scope of the invention in any way.

FORMULATION EXAMPLE

Tablets each containing 0.3 mg of active ingredient are made as follows:

| | |
|---|---|
| Moxonidine | 0.300 mg |
| Lactose | 95.700 mg |
| Povidone | 0.700 mg |
| Crospovidone | 3.000 mg |
| Magnesium stearate | 0.300 mg |
| Hydroxypropyl methylcellulose 2910 | 1.300 mg |
| Ethylcellulose Aqueous | 1.200 mg |
| Polyethyene Glycol 6000 | 0.250 mg |
| Talc | 0.975 mg |
| Red Ferric Oxide | 0.025 mg |
| Titanium Dioxide | 1.250 mg |
| Total | 105 mg |

The particular dose of moxonidine administered according to this invention will of course be determined by the particular circumstances surrounding the case, including the warm blooded mammal being treated, the route of administration, the particular condition being treated, and similar considerations. The compound can be administered by a variety of routes including oral, rectal, transdermal, subcutaneous, intravenous, intramuscular, or intranasal routes. Alternatively, the compound may be administered by continuous infusion. A typical daily dose will contain from 0.005 mg to 5.0 mg of moxonidine. Preferably, daily doses will be 0.01 mg to 3.0 mg, more preferably from 0.05 mg to 2.0 mg.

According to the invention, moxonidine may be administered to the warm blooded mammal before, with or after administration of the agent. Conveniently, it may be administered with the agent being potentiated in a single pharmaceutical composition.

According to another aspect, the present invention provides a pharmaceutical composition, which comprises moxonidine and an agent which is selected from a serotonin re-uptake inhibitor, a norepinephrine re-uptake inhibitors, both a serotonin and norepinephrine re-uptake inhibitor, and an atypical antidepressant, together with a pharmaceutically acceptable diluent or carrier.

The dose at which the agent is administered will depend upon the particular agent selected, and may readily be determined by those skilled in the art, for example, the dose at which fluoxetine is administered may typically be in the range of from 10 to 80 mg/day.

The potentiating effect of moxonidine on the a antidepressant action of fluoxetine is demonstrated by the following clinical trial.

Patients aged 18 to 65 with major depression as defined in the Diagnostic and Statistical Manual of Mental Disorders, Fourth Edition (DSM-IV) are either dosed with fluoxetine 20 mg daily and moxonidine 0.2 mg twice daily, increasing after one week to fluoxetine 20 mg daily and moxonidine 0.3 mg twice daily, or fluoxetine 20 mg daily and placebo twice daily in a double-blind, randomized clinical trial. The time to onset of action, and the percentage of patients responding to fluoxetine treatment with and without co-administration of moxonidine is then determined.

An accepted standard for detecting and comparing the antidepressant activity of different classes of antidepression compounds for which there is a good correlation with human antidepression activity is the forced swim test model as described by Cervo et al. (1992) in Neuropharmacology, vol. 31, pp. 331–335. The potentiating effect of moxonidine on a particular serotonin re-uptake inhibitor, a norepinephrine re-uptake inhibitors, both a serotonin and norepinephrine re-uptake inhibitor, or an atypical antidepressant may be evaluated using the forced swim test model.

The forced swim test (FST) in mice is a relatively rapid in vivo screen for detecting antidepressant-like compounds in vivo. It is sensitive to compounds from the monoamine oxidase inhibitor and tricyclic antidepressant classes, but is much less sensitive to selective serotonin reuptake inhibitors, see, for example, Porsolt et al, 1991, Adv in Pharm. Sci, pp 137–159. Several compounds are active in this test whose antidepressant efficacy has yet to be established. Moxonidine in addition to its activity at α2 receptors is also an imidazoline imidazoline ligand. We compared the effects of moxonidine with some known Imidazoline ligands in the FST to determine if affinity for this site was associated with an antidepressant-like profile in this test.

METHODS

Female BKTO (Bantin Kingman Tuck Outbred) mice (Bantin and Kingman, Hull, England) were housed in groups of 15. Animals were kept in the holding facility for two weeks after arrival before experimental use. Animals were 25–35g at time of use. Immobility was measured in 11 beakers with 600 ml of water (23° C.) i.e. 10 cm deep. Time spent immobile was measured with a stopwatch.

Moxonidine, imipramine, fluoxetine, and idazoxan (Research Biochemicals International, Massachusetts, USA) were all made up in b-cyclodextrin. All compounds were injected sc in a volume of 10 ml/kg. Drug treatment bottles were coded so that the observer was unaware of the dose of treatment the animals had received. A positive control of imipramine (10 mg/kg) was included in all dose response studies.

PROCEDURE

Animals were removed from their home cages and placed in individual holding cages (10×15×13 cm) for at least 60 mins prior to the beginning of the experiment.

Mice were dosed with the test compound and then returned to the holding cages for 30 mins. When the pre-treatment time had elapsed, the animals were placed in the beakers and the time spent immobile was recorded. Where drug interactions were being examined, the animals received their first treatment and were then returned to the holding cages for 30 mins. When this time had elapsed the animals received the second treatment and were then returned to the holding cages for a further 30 mins before being tested.

The animals were placed in the beakers and activity measured for 5 mins. Immobility was measured only for the last 4 minutes as all animals swam for the first minute irrespective of treatment. Each group was made up of a minimum of 6 subjects.

Data Analysis

Data were analysed by ANOVA and significant differences were determined by the Least Square Means test for post hoc analysis.

RESULTS

In the following tables, V is vehicle, M is moxonidine, and I is imipramine.

TABLE 1

The effect of Moxonidine (2.5–10 mg/kg s.c.) on immobility in the FST in mice. Data are mean time spent immobile in the FST for each group. Significant differences were determined by Least Square Mean test following significant One-Way Anova.
$p < 0.001, *p < 0.001$ vs Vehicle control.

| DOSE mg/kg | Immobility in secs. | SEM |
|---|---|---|
| V | 179 | 9.4 |
| 2.5 | 57.4 | 14*** |
| 5 | 40.7 | 21*** |
| 10 | 92.4 | 22*** |
| 10/IMI | 101 | 5.5** |

TABLE 2

The effect of idazoxan (0.3125–0.125 mg/kg s.c.) vs. Moxonidine (5 mg/kg) on immobility in the FST in mice. Data are mean time spent immobile in the FST for each group. Significant differences were determined by Least Square Mean test following significant One-Way Anova. $p < 0.001, *p < 0.001$ vs Vehicle/Vehicle (V/V) control. $++p < 0.01, +++p < 0.001$ vs Vehicle/Moxonidine (V/M) group.

| IDAZOXAN mg/kg | Immobility secs. | SEM |
|---|---|---|
| V/V | 188 | 8 |
| V/MOX | 63.4 | 13*** |
| 0.03/MOX | 155 | 19+++ |
| 0.06/MOX | 119 | 20++ |
| 0.12/MOX | 172 | 8.9+++ |

TABLE 3

The effect of Moxonidine (0.06–0.25 mg/kg s.c.) vs. Imipramine (1 mg/kg) on immobility in the FST in mice. Data are mean time spent immobile in the FST for each group. Bars are sem. Significant differences were determined by Least Square Mean test following significant One-Way Anova. $*p < 0.05, ***p < 0.001$ vs Vehicle/Vehicle (V/V) control. $++p < 0.01$, vs Vehicle/Imipramine (V/I) group.

| MOXONIDINE mg/kg | Immobility sec. | SEM |
|---|---|---|
| V/V | 197 | 13 |
| V/IMI | 111 | 15 |
| 0.06/IMI | 146 | 12* |
| 0.12/IMI | 172 | 16 |
| 0.25/IMI | 106 | 11**++ |

TABLE 4

The effect of Moxonidine (0.25–1 mg/kg s.c.) vs. Fluoxetine (3 mg/kg) on immobility in the FST in mice. Data are mean time spent immobile in the FST for each group. Bars are sem. No significant effect of any treatment was detected.

| MOXONIDINE mg/kg | Immobility secs. | SEM |
|---|---|---|
| V/V | 153 | 17 |
| V/FLX | 156 | 19 |
| 0.25/FLX | 128 | 25 |
| 0.5/FLX | 127 | 23 |
| 1/FLX | 159 | 13 |

The FST test is generally regarded as being insensitive to serotonin re-uptake inhibitors. This was confirmed in that moxonidine enhanced the effects of imipramine, a typical tricyclic antidepressant, but had no effect in combination with a dose of fluoxetine. Considering test's insensitivity to serotonin re-uptake inhibitors, the potentiating effect of moxonidine on serotonin re-uptake inhibitors is not fully demonstrated. In view of these results and moxonidine's unique properties, the potentiating effect of moxonidine on serotonin re-uptake inhibitors is still expected.

We claim:

1. A pharmaceutical composition, which comprises moxonidine, or a pharmaceutically acceptable salt thereof and an agent which is selected from a serotonin re-uptake inhibitor, a norepinephrine re-uptake inhibitors, both a serotonin and norepinephrine re-uptake inhibitor, and an atypical antidepressant, together with a pharmaceutically acceptable diluent or carrier.

2. A pharmaceutical composition, comprising moxonidine, or a pharmaceutically acceptable salt thereof, and an agent selected from fluoxetine, citalopram, fluvoxamine, paroxetine, sertraline, tomoxetine, reboxatine, duloxetine, venlafaxine and milnacipran.

3. A pharmaceutical composition, comprising moxonidine, or a pharmaceutically acceptable salt thereof, and fluoxetine.

4. A method for potentiating a therapeutic action of an agent selected from a serotonin re-uptake inhibitor, a norepinephrine re-uptake inhibitors, a serotonin and norepinephrine re-uptake inhibitor, and an atypical antidepressant in a warm blooded mammal requiring such treatment, which comprises administering to said mammal an effective amount of moxonidine, or a pharmaceutically acceptable salt thereof and an effective amount of a serotonin re-uptake inhibitor, a norepinephrine re-uptake inhibitors, a serotonin and norepinephrine re-uptake inhibitor, or an atypical antidepressant.

5. A method as claimed in claim 4, in which said therapeutic action is antidepressant, antibulimia, antipremenstrual syndrome, antiobsessive-compulsive disease, antiobesity or antiurinary incontinence action.

6. A method as claimed in claim 4, in which said agent is a serotonin and norepinephrine re-uptake inhibitor.

7. A method as claimed in any one of claims 4 to 6, in which said therapeutic action is an antidepressant action.

8. A method for treating depression in a warm blooded mammal requiring treatment, which comprises administering an effective amount of fluoxetine and an effective amount of moxonidine, or a pharmaceutically acceptable salt thereof.

9. A method of claim 4 in which said agent is selected from fluoxetine, citalopram, fluvoxamine, paroxetine, sertraline, tomoxetine, reboxatine, duloxetine, venlafaxine and milnacipran.

10. A method of claim 5 in which said agent is selected from fluoxetine, citalopram, fluvoxamine, paroxetine, sertraline, tomoxetine, reboxatine, duloxetine, venlafaxine and milnacipran.

11. A method of claim 6 in which said agent is selected from fluoxetine, citalopram, fluvoxamine, paroxetine, sertraline, tomoxetine, reboxatine, duloxetine, venlafaxine and milnacipran.

12. A method of claim 7 in which said agent is selected from fluoxetine, citalopram, fluvoxamine, paroxetine, sertraline, tomoxetine, reboxatine, duloxetine, venlafaxine and milnacipran.

13. A method of claim 9 in which said agent is fluoxetine.

14. A method of claim 10 in which said agent is fluoxetine.

15. A method of claim 11 in which said agent is fluoxetine.

16. A method of claim 12 in which said agent is fluoxetine.

17. A method of claim 4 in which said warm blooded mammal is a human.

18. A method of claim 5 in which said warm blooded mammal is a human.

19. A method of claim 6 in which said warm blooded mammal is a human.

20. A method of claim 7 in which said warm blooded mammal is a human.

21. A method of claim 9 in which said warm blooded mammal is a human.

22. A method of claim 10 in which said warm blooded mammal is a human.

23. A method of claim 11 in which said warm blooded mammal is a human.

24. A method of claim 12 in which said warm blooded mammal is a human.

25. A method of claim 13 in which said warm blooded mammal is a human.

26. A method of claim 14 in which said warm blooded mammal is a human.

27. A method of claim 15 in which said warm blooded mammal is a human.

28. A method of claim 16 in which said warm blooded mammal is a human.

* * * * *